US009872320B2

(12) United States Patent
Jun

(10) Patent No.: US 9,872,320 B2
(45) Date of Patent: Jan. 16, 2018

(54) METHOD OF CONTROLLING A MEDICAL APPARATUS AND MOBILE APPARATUS THEREFOR

(71) Applicant: SAMSUNG ELECTRONICS CO., LTD., Suwon-si (KR)

(72) Inventor: Yoon-woo Jun, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 373 days.

(21) Appl. No.: 14/580,619

(22) Filed: Dec. 23, 2014

(65) Prior Publication Data

US 2015/0181629 A1 Jun. 25, 2015

(30) Foreign Application Priority Data

Dec. 23, 2013 (KR) ........................ 10-2013-0161786

(51) Int. Cl.
*H04W 76/02* (2009.01)
*H04W 12/08* (2009.01)
(Continued)

(52) U.S. Cl.
CPC ............. *H04W 76/021* (2013.01); *A61B 5/00* (2013.01); *A61B 5/0015* (2013.01); *A61B 6/4405* (2013.01); *A61B 6/4494* (2013.01); *A61B 6/462* (2013.01); *A61B 6/464* (2013.01); *A61B 6/465* (2013.01); *A61B 6/467* (2013.01); *A61B 6/468* (2013.01); *A61B 6/548* (2013.01); *A61B 6/563* (2013.01); *A61B 8/0825* (2013.01); *A61B 8/4405* (2013.01); *A61B 8/4438* (2013.01); *A61B 8/462* (2013.01); *A61B 8/464* (2013.01); *A61B 8/467* (2013.01); *A61B 8/468* (2013.01);
(Continued)

(58) Field of Classification Search
USPC .......................................................... 715/771
See application file for complete search history.

(56) References Cited

U.S. PATENT DOCUMENTS

| | | | | |
|---|---|---|---|---|
| 6,704,007 | B1 * | 3/2004 | Clapper | G06F 1/1616 345/204 |
| 8,401,661 | B2 * | 3/2013 | Vamos | A61N 1/37264 607/60 |

(Continued)

FOREIGN PATENT DOCUMENTS

| | | | |
|---|---|---|---|
| KR | 10-2007-0036894 | A | 4/2007 |
| WO | 2013077887 | A1 | 5/2013 |
| WO | 2013/125801 | A1 | 8/2013 |

OTHER PUBLICATIONS

Communication dated Mar. 6, 2015 by the International Searching Authority in related Application No. PCT/KR2014/012708, (PCT/ISA/210 & PCT/ISA/237).

(Continued)

*Primary Examiner* — Reza Nabi
(74) *Attorney, Agent, or Firm* — Sughrue Mion, PLLC

(57) ABSTRACT

A method of controlling a medical apparatus which includes: establishing, by a mobile apparatus, a communication link between the mobile apparatus and the medical apparatus; when the communication link is established, detecting an operation mode of the mobile apparatus; determining a function corresponding to the detected operation mode from functions provided by the medical apparatus; and performing the determined function.

9 Claims, 10 Drawing Sheets

(51) Int. Cl.

| | |
|---|---|
| ***G06F 19/00*** | (2011.01) |
| ***A61B 6/00*** | (2006.01) |
| ***A61B 8/08*** | (2006.01) |
| ***A61B 8/00*** | (2006.01) |
| ***H04W 12/06*** | (2009.01) |
| ***A61B 90/90*** | (2016.01) |
| ***A61B 90/98*** | (2016.01) |
| *A61B 5/00* | (2006.01) |
| *A61B 5/055* | (2006.01) |
| *H04W 88/02* | (2009.01) |
| *H04M 1/725* | (2006.01) |
| *A61B 34/00* | (2016.01) |

(52) U.S. Cl.

CPC ................ *A61B 8/54* (2013.01); *A61B 8/565* (2013.01); *A61B 90/90* (2016.02); *A61B 90/98* (2016.02); *G06F 19/3406* (2013.01); *G06F 19/3418* (2013.01); *H04W 12/06* (2013.01); *H04W 12/08* (2013.01); *A61B 5/004* (2013.01); *A61B 5/055* (2013.01); *A61B 5/74* (2013.01); *A61B 34/25* (2016.02); *A61B 2560/045* (2013.01); *H04M 1/72533* (2013.01); *H04W 88/02* (2013.01)

(56) References Cited

U.S. PATENT DOCUMENTS

2008/0229175 A1* 9/2008 Jun ...................... G06F 9/4446 714/759
2008/0319510 A1* 12/2008 Simpson ............ A61N 1/37235 607/59
2009/0037224 A1* 2/2009 Raduchel .............. G06F 19/322 705/3
2009/0099866 A1* 4/2009 Newman ............... G06F 19/327 705/2
2010/0010330 A1* 1/2010 Rankers ............. A61B 5/14532 600/365
2010/0131294 A1* 5/2010 Venon ................... G06F 19/321 705/3
2010/0323762 A1* 12/2010 Sindhu .................. G06F 1/1613 455/566
2011/0105955 A1* 5/2011 Yudovsky ........... G01P 15/0802 600/595
2011/0118562 A1 5/2011 Smith et al.
2011/0270096 A1* 11/2011 Osorio ............... A61B 5/02405 600/483
2011/0282688 A1* 11/2011 Raggousis ............ G06F 19/322 705/3
2012/0233565 A1* 9/2012 Grant .................... G06F 3/0483 715/776
2012/0262370 A1* 10/2012 Ko ...................... G06F 3/03547 345/157
2013/0009867 A1* 1/2013 Woo ........................ G09G 5/00 345/156
2013/0109929 A1 5/2013 Menzel
2013/0141366 A1 6/2013 Ritter et al.
2013/0184587 A1 7/2013 Eom et al.
2013/0201222 A1* 8/2013 Doyle ................. G06F 19/3406 345/672
2013/0210365 A1* 8/2013 Karuppiah .......... G06F 19/3418 455/63.1
2013/0222275 A1* 8/2013 Byrd .................. G06F 3/04883 345/173
2014/0187934 A1* 7/2014 Urness .................. G06Q 10/10 600/437
2014/0325360 A1* 10/2014 Jung ..................... G06F 3/0482 715/728
2014/0337149 A1* 11/2014 Ke ......................... G06F 3/017 705/15
2015/0025386 A1* 1/2015 Ninomiya ............ A61B 8/4427 600/443
2015/0180917 A1* 6/2015 Im ...................... H04N 5/23222 348/14.01
2015/0181629 A1* 6/2015 Jun ..................... H04W 76/021 455/420
2016/0110507 A1* 4/2016 Abbo ........................ G06F 8/61 705/3
2016/0113626 A1* 4/2016 Lee ...................... A61B 5/0035 600/440
2016/0113627 A1* 4/2016 Lee ........................ A61B 8/468 600/440
2016/0142637 A1* 5/2016 Nuggehalli .......... A61B 5/0077 348/333.02
2016/0157825 A1* 6/2016 Lee ...................... A61B 8/5215 600/437
2016/0170636 A1* 6/2016 Lee ..................... G06F 3/04817 715/773
2016/0174944 A1* 6/2016 Song .................... A61B 8/5215 600/453
2016/0267238 A1* 9/2016 Nag .................... G06F 19/3418
2016/0306930 A1* 10/2016 Zavaleta ............... E05D 7/0423
2016/0350503 A1* 12/2016 Jun ..................... G06F 19/3406

OTHER PUBLICATIONS

Communication issued by the European Patent Office dated Sep. 14, 2017 in counterpart European Patent Application No. 14875717.2.

* cited by examiner

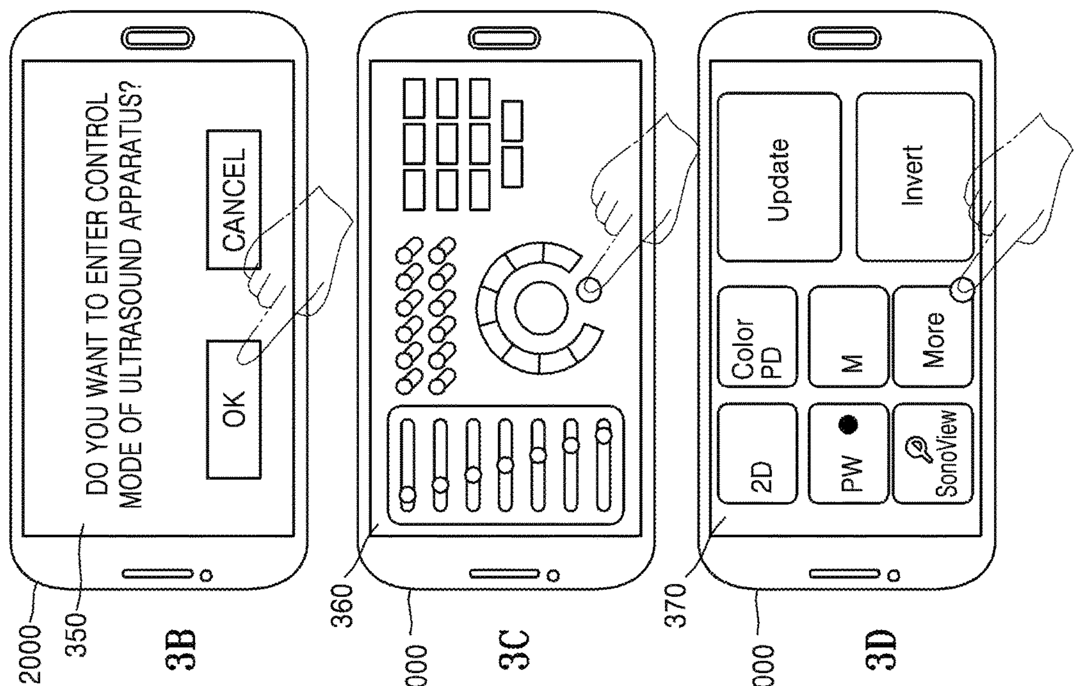
FIG. 3B
FIG. 3C
FIG. 3D
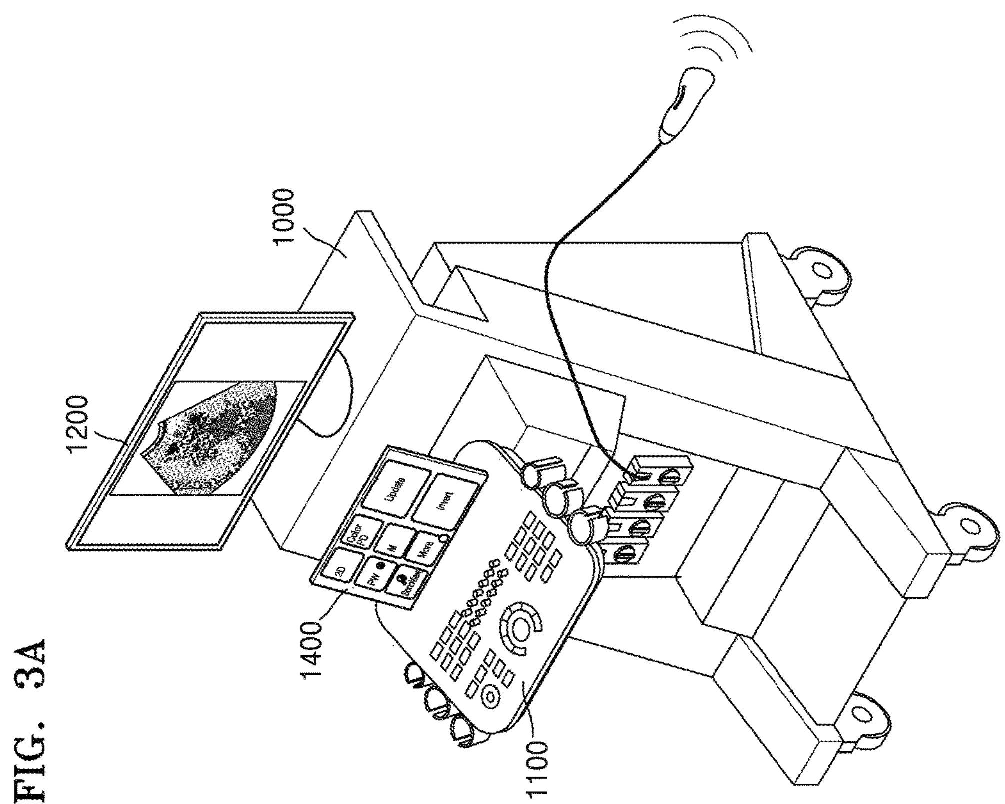
FIG. 3A

FIG. 7A
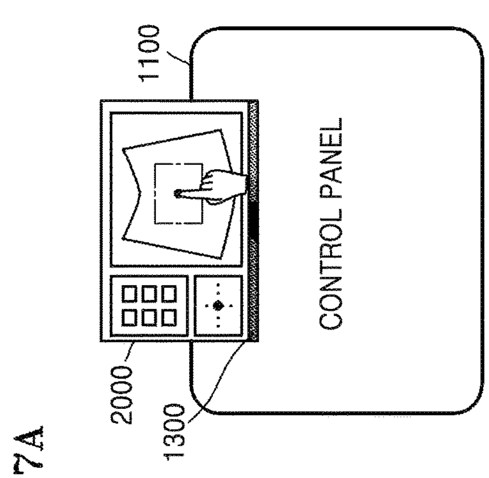
FIG. 7B
1300
2000
1100
CONTROL PANEL
FIG. 7C
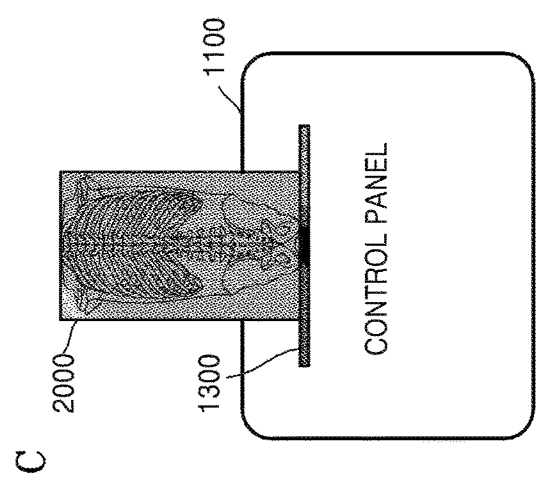
FIG. 7D
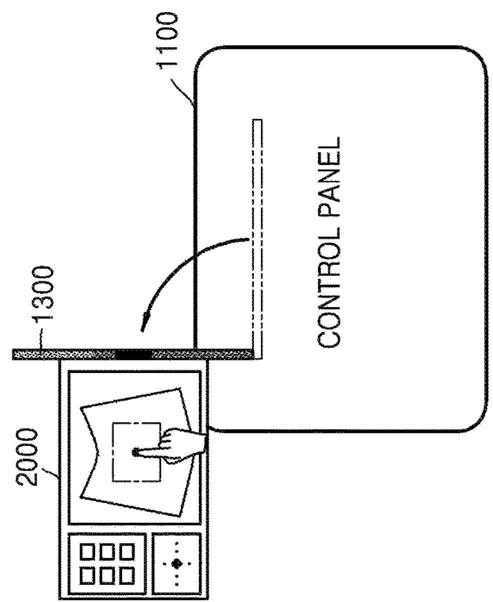

METHOD OF CONTROLLING A MEDICAL APPARATUS AND MOBILE APPARATUS THEREFOR

CROSS-REFERENCE TO RELATED APPLICATION

This application claims priority from Korean Patent Application No. 10-2013-0161786, filed on Dec. 23, 2013, in the Korean Intellectual Property Office, the disclosure of which is incorporated herein in its entirety by reference.

BACKGROUND

1. Field

Apparatuses and methods consistent with exemplary embodiments relate to a method of controlling a medical apparatus and a mobile apparatus therefor.

2. Description of the Related Art

According to development of wire and wireless communication networks, mobile apparatuses may output visual data to be recognizable by users by displaying the data on screens. Since communication performances as well as display resolutions of the mobile apparatuses have been increased, various types of content are displayable by the mobile apparatuses.

Also, medical apparatuses may perform wired communication as well as wireless communication including near distance and/or long distance wireless communication with an external device.

However, since medical apparatuses, such as ultrasound apparatuses, X-ray apparatuses, computed tomography (CT) apparatuses, and magnetic resonance imaging (MRI) apparatuses, have low mobility, it is inconvenient to diagnose the users who move and/or travel. In addition, due to various constraints of display apparatuses included in the medical apparatuses, it is difficult to display various types of information.

SUMMARY

One or more exemplary embodiments provide a method of increasing usability of a medical apparatus by connecting a mobile apparatus to the medical apparatus, and the mobile apparatus using the method.

Additional aspects will be set forth in part in the description which follows and, in part, will be apparent from the description, or may be learned by practice of the exemplary embodiments.

According to an aspect of an exemplary embodiment, a method of performing a function includes: forming, by a mobile apparatus, a communication link between the mobile apparatus and a medical apparatus; when the communication link is formed, detecting an operation mode of the mobile apparatus; determining at least one function corresponding to the detected operation mode from among functions provided by the medical apparatus; and performing the determined at least one function.

The determining of the at least one function may include: receiving identification (ID) information of the medical apparatus from the medical apparatus, through the communication link; and determining the at least one function by considering the received ID information of the medical apparatus.

The detecting of the operation mode may include determining whether the operation mode is a width direction mode or a height direction mode based on displacement information of the mobile apparatus.

The performing of the determined at least one function may include, when the operation mode is the width direction mode, controlling the medical apparatus based on a user input.

The performing of the determined at least one function may include, when the operation mode is the height direction mode, displaying object-related information including at least one of medical record information of an object, medical image record information of the object, a medical image captured by the medical apparatus, and lesion information of the object.

The method may further include: receiving an input for changing the operation mode of the mobile apparatus; changing the operation mode of the mobile apparatus to another operation mode based on the input; and performing at least one function corresponding to the other operation mode.

The performing of the determined at least one function may include: displaying a confirmation button for confirming whether to perform the determined at least one function; and performing the determined at least one function based on a user's selection regarding the confirmation button.

According to an aspect of an exemplary embodiment, a mobile apparatus includes: a communicator that forms a communication link with a medical apparatus; when the communication link is formed, a sensor that detects an operation mode; and a controller that determines at least one function corresponding to the detected operation mode from among functions provided by the medical apparatus, and performs the determined at least one function.

The controller may receive identification (ID) information of the medical apparatus from the medical apparatus through the communication link, and determine the at least one function by considering the received ID information of the medical apparatus.

The sensor may determine whether the operation mode of the mobile apparatus is a width direction mode or a height direction mode based on displacement information of the mobile apparatus.

When the operation mode of the mobile apparatus is the width direction mode, the controller may perform a function of controlling the medical apparatus based on a user input.

When the operation mode of the mobile apparatus is the height direction mode, the controller may display object-related information including at least one of medical record information of an object, medical image record information of the object, a medical image captured by the medical apparatus, and lesion information of the object.

The sensor may receive an input for changing the operation mode of the mobile apparatus and change the operation mode of the mobile apparatus to another operation mode based on the input, and the controller may perform at least one function corresponding to the other operation mode.

The controller may display a confirmation button for confirming whether to perform the determined at least one function, and perform the determined at least one function based on a user's selection regarding the confirmation button.

According to an aspect of an exemplary embodiment, a non-transitory computer-readable recording medium has recorded thereon a program, which, when executed by a computer, causes the computer to perform the method.

According to an aspect of an exemplary embodiment, a mobile apparatus for controlling a medical imaging apparatus includes: a processor that implements a communicator configured to communicate with the medical imaging apparatus and receive information of the medical imaging apparatus, from the medical imaging apparatus and a controller that performs a control operation of the medical imaging apparatus based on the received information.

The information of the medical imaging apparatus comprises at least one of a type, a model name, and identification (ID) information of the medical imaging apparatus.

The mobile apparatus further comprising: a display that displays a graphical user interface (GUI) configured to control the medical imaging apparatus based on the received information, wherein the controller may perform the control operation of the medical imaging apparatus according to a user input received via the GUI.

The controller may perform the control operation of the medical imaging apparatus further based on displacement information of the mobile apparatus.

The controller may perform a function of controlling the medical imaging apparatus according to a user input based on the received information, in response to a displacement in a first direction in which the mobile apparatus is elongated, and perform a function of displaying a medical image captured by the medical imaging apparatus, in response to a displacement in a second direction perpendicular to the first direction.

BRIEF DESCRIPTION OF THE DRAWINGS

The above and/or other aspects will become more apparent by describing certain exemplary embodiments with reference to the accompanying drawings, in which:

FIGS. 3A, 3B, 3C, and 3D are diagrams for describing a method of controlling a medical apparatus according to an operation mode of a mobile apparatus, according to an exemplary embodiment;

FIGS. 7A, 7B, 7C, and 7D are diagrams for describing a method of determining a function to be performed according to displacement of a mobile apparatus, according to exemplary embodiments;

DETAILED DESCRIPTION

Figure 1:
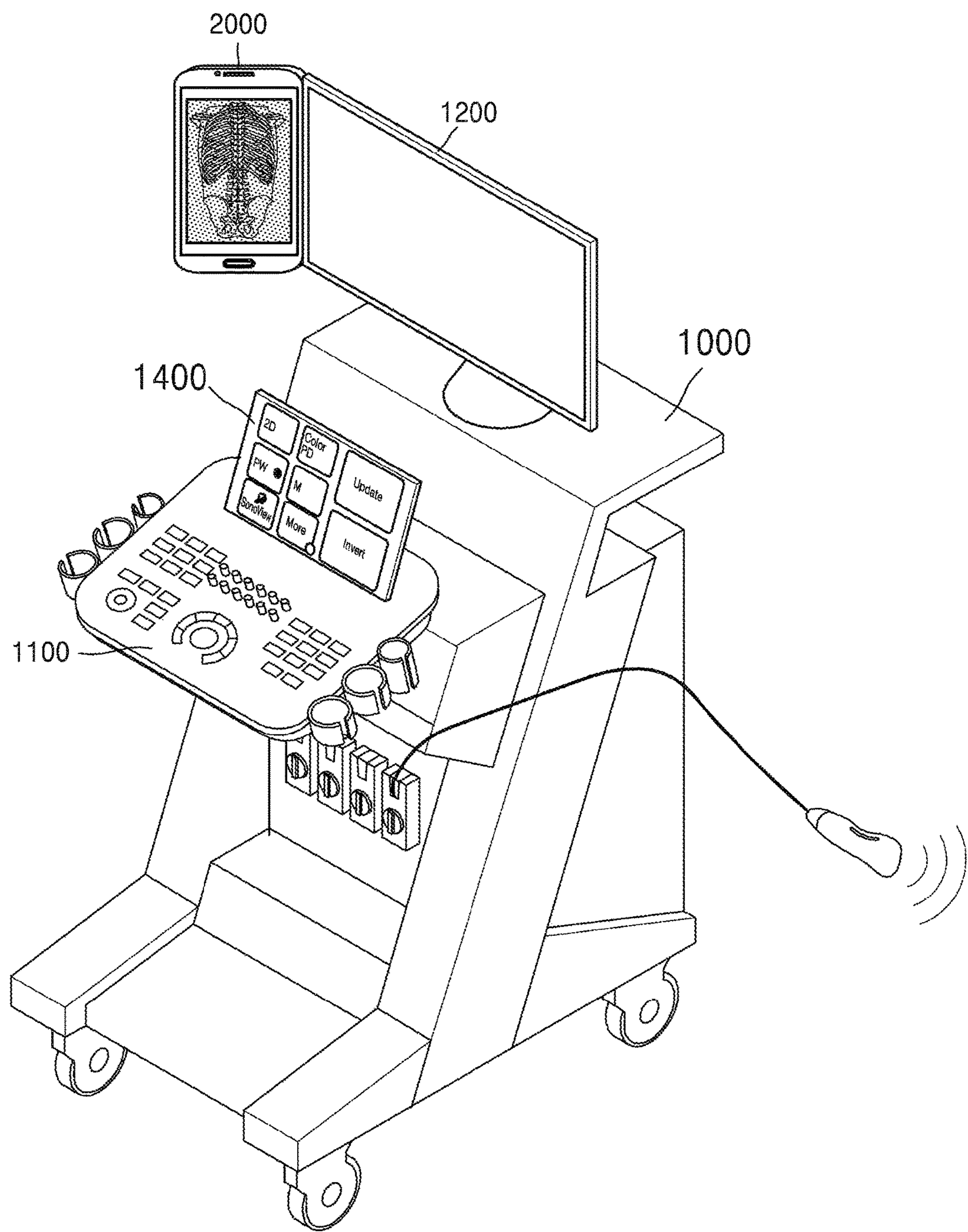
FIG. 1 is a diagram for describing a system in which a mobile apparatus and a medical apparatus interwork with each other, according to an exemplary embodiment.

Certain exemplary embodiments are described in greater detail below with reference to the accompanying drawings.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected, and in this case, the meaning of the selected terms will be described. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or a combination thereof.

Reference will now be made in detail to exemplary embodiments, which are illustrated in the accompanying drawings. In this regard, the exemplary embodiments may have different forms and should not be construed as being limited to the descriptions set forth herein. In the following description, well-known functions or constructions are not described in detail so as not to obscure the embodiments with unnecessary detail. Also, in drawings, like reference numerals denote like elements.

FIG. 1 is a diagram illustrating a system in which a mobile apparatus 2000 and a medical apparatus 1000 interwork with each other, according to an exemplary embodiment.

As shown in FIG. 1, the mobile apparatus 200 may interwork with the medical apparatus 1000 to perform various functions.

The mobile apparatus 2000 may control the medical apparatus 1000 according to a user input by being connected to the medical apparatus 1000. The mobile apparatus 2000 may display a graphical user interface (GUI) for controlling the medical apparatus 1000, and transmit control information to the medical apparatus 1000 according to a user input received through the GUI.

Also, the mobile apparatus 2000 may display object-related information by being connected to the medical apparatus 1000. The mobile apparatus 2000 may display information about an object of which an image is being captured or diagnosed by the medical apparatus 1000. The object-related information may include identification (ID) information, a medical record, a medical image, and information needed to diagnose a lesion of an object.

Also, the mobile apparatus 2000 may change a function to be performed according to an operation mode of the mobile apparatus 200. The mobile apparatus 2000 may include, for example, a displacement sensor, and perform a preset function according to displacement of the mobile apparatus 2000 sensed by the displacement sensor. An operation mode may be determined according to the displacement of the mobile apparatus 2000. Also, a function to be performed according to an operation mode may be preset in the mobile apparatus 2000.

The mobile apparatus 2000 may be a mobile phone, a smart phone, a laptop computer, a tablet personal computer (PC), an electronic book terminal, a digital broadcasting terminal, a personal digital assistant (PDA), a portable multimedia player (PMP), an MPEG audio layer-3 (MP3) player, a digital camera, or a navigation device, but is not limited thereto.

The mobile apparatus 2000 and the medical apparatus 1000 may be connected via wires. The mobile apparatus 2000 and the medical apparatus 1000 may each include a port that is connectable to another apparatus via wires.

Also, the mobile apparatus 2000 and the medical apparatus 1000 may be connected via short-range wireless communication, such as Bluetooth communication, Bluetooth low energy (BLE) communication, near field communication (NFC), wireless local area network (WLAN) (e.g., Wi-Fi) communication, Zigbee communication, infrared data association (IrDA) communication, Wi-Fi direct (WFD) communication, ultra wideband (UWB) communication, or Ant+ communication, but is not limited thereto. For example, the mobile apparatus 2000 and the medical apparatus 1000 may be connected via long distance wireless communication.

Also, the mobile apparatus 2000 may transmit and/or receive a wireless signal to and/or from at least one of a base station, an external terminal, and a server, via a mobile communication network. Here, the wireless signal may include any type of data according to transmission and/or reception of a voice call signal, a video call signal, or a text and/or multimedia message.

Also, the mobile apparatus 2000 and the medical apparatus 1000 may perform wired or wireless communication with a server in which medical-related information is stored. The server in which the medical-related information is stored may include, for example, a picture archiving and communication system (PACS), an electronic medical record (EMR), a personal health record (PHR), or a radiology information system (RIS).

The medical apparatus 1000 may be controlled by the mobile apparatus 2000. The medical apparatus 1000 may operate based on control information received from the mobile apparatus 1000. Also, the medical apparatus 1000 may transmit the object-related information to the mobile apparatus 2000 based on a request from the mobile apparatus 2000.

The medical apparatus 1000 may include a medical image capturing apparatus, such as an ultrasound apparatus, an X-ray apparatus, a computed tomography (CT) apparatus, or a magnetic resonance imaging (MRI) apparatus, and may further include a console apparatus, such as a desktop, which controls the medical image capturing apparatus. Also, the medical apparatus 1000 may include a medical image display apparatus.

The medical apparatus 1000 may include a control panel 1100 of 1400 for controlling the medical apparatus 1000 via physical buttons, and a display 1200 that displays an image captured by the medical apparatus 1000 or a GUI for controlling the medical apparatus 1000.

A docking system (not shown) may be included on the control panel 1100 or at a side of the display 1200. The mobile apparatus 2000 may be mounted on the docking system of the medical apparatus 1000 to be connected to the medical apparatus 1000 via wires.

Figure 2:
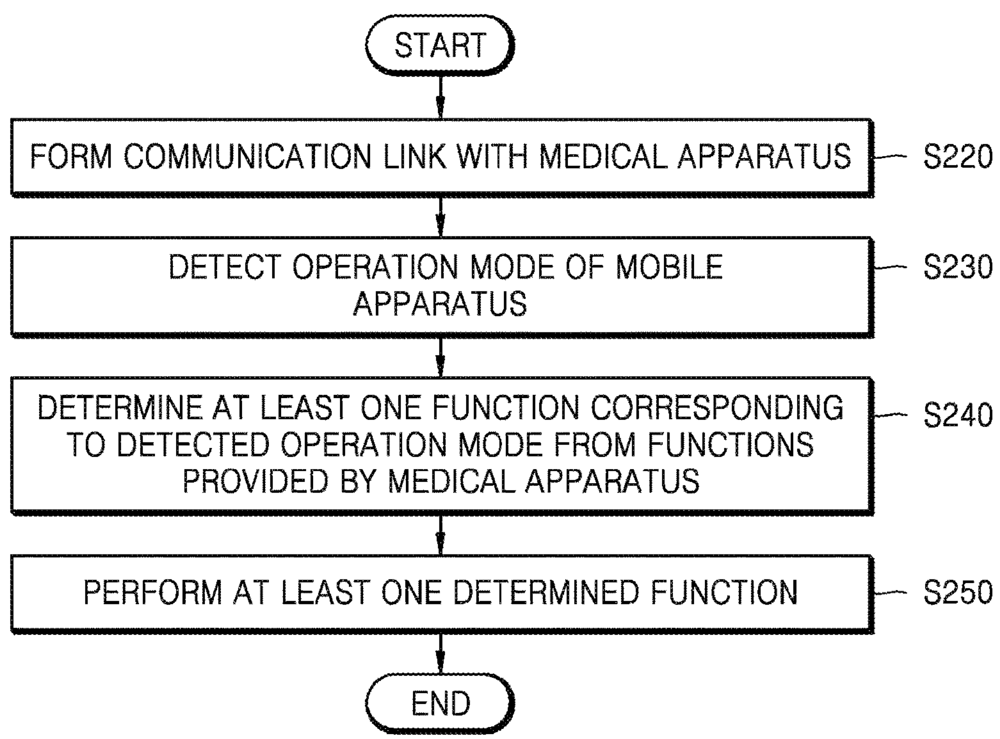
FIG. 2 is a flowchart of a method of controlling a medical apparatus by using a mobile apparatus, according to an exemplary embodiment.

FIG. 2 is a flowchart of a method of controlling the medical apparatus 1000, according to an exemplary embodiment.

In operation S220, the mobile apparatus 2000 may form a communication link with the medical apparatus 1000.

The mobile apparatus 2000 may be connected to the medical apparatus 1000 via any one of various wireless communications. For example, if the mobile apparatus 2000 and the medical apparatus 1000 each include an NFC module, the NFC module of the mobile apparatus 2000 and the NFC module of the medical apparatus 1000 may operate in a peer-to-peer (P2P) mode. The mobile apparatus 2000 may be tagged by the NFC module of the medical apparatus 1000 when the NFC module (i.e., a client) of the mobile apparatus 2000 accesses the NFC module (i.e., a host) of the medical apparatus 1000. The mobile apparatus 2000 may form the communication link with the medical apparatus 1000 by being tagged to the medical apparatus 1000.

Also, the mobile apparatus 2000 may be connected to the medical apparatus 1000 via wires. The mobile apparatus 2000 may be connected to the medical apparatus 1000 via wires by using, for example, a port, an expansion slot, or a network interface (such as local area network (LAN)) of the medical apparatus 1000.

Even after the mobile apparatus 2000 forms the communication link with the medical apparatus 1000, the mobile apparatus 2000 may perform a unique function of the mobile apparatus 2000, for example, outputting an image, a voice, or text information or schedule information.

In an exemplary embodiment, if the mobile apparatus 2000 forms the communication link with the medical apparatus 1000, the mobile apparatus 2000 may operate dependently upon the medical apparatus 1000. In other words, the mobile apparatus 2000 may perform only a function of controlling the medical apparatus 1000. In another exemplary embodiment, even if the mobile apparatus 2000 operates dependently upon the medical apparatus 1000, some functions of the mobile apparatus 2000 may be set to be operable by the mobile apparatus 2000.

In operation S230, the mobile apparatus 2000 may detect an operation mode of the mobile apparatus 2000 in response to the forming of the communication link.

When the communication link is formed, the mobile apparatus 2000 may activate a module for detecting an operation mode of the mobile apparatus 2000. For example, when the communication link is formed, the mobile apparatus 2000 may detect an operation mode of the mobile apparatus 2000 by using the displacement sensor included in the mobile apparatus 2000.

Examples of an operation mode of the mobile apparatus 2000 may include a width direction mode and a height direction mode. For example, the width direction mode may be a state in which a screen of the mobile apparatus 2000 is elongated in a width direction with respect to the ground, and the height direction mode may be a state in which the screen of the mobile apparatus 2000 is elongated in a length direction with respect to the ground.

The mobile apparatus 2000 may detect the displacement of the mobile apparatus 2000 by using a motion sensor, such as an accelerometer, a gravity sensor, a gyroscope, or a rotational vector sensor, and/or a position sensor, such as an orientation sensor or a magnetometer, but is not limited thereto.

In operation S240, the mobile apparatus 2000 may determine at least one function corresponding to the detected operation mode from among functions provided by the medical apparatus 1000.

For example, according to an exemplary embodiment, if an operation mode is a width direction mode, the mobile apparatus 2000 may determine to perform a function for controlling the medical apparatus 1000 with which the communication link is formed. Also, according to an exemplary embodiment, if an operation mode is a height direction mode, the mobile apparatus 2000 may determine to perform a function of displaying the object-related information about the object of which an image is being captured or displayed by the medical apparatus 1000.

In another example, if an operation mode is a width direction mode, the mobile apparatus 2000 may determine to perform a function of displaying the object-related information about the object of which an image is being captured or displayed by the medical apparatus 1000. Also, if an operation mode is a height direction mode, the mobile apparatus 2000 may determine to perform a function of controlling the medical apparatus 1000 with which the communication link is formed.

According to an exemplary embodiment, the mobile apparatus 2000 may determine at least one function by further considering ID information of the medical apparatus 1000. The ID information of the medical apparatus 1000 may include a type, a mode name, and an intrinsic identifier of the medical apparatus 1000. The mobile apparatus 2000 may receive the ID information of the medical apparatus 1000 from the medical apparatus 1000 through the communication link.

For example, the mobile apparatus 2000 may execute a control module of the medical apparatus 1000, which is preset according to a type or model name of the medical apparatus 10000. Also, the mobile apparatus 2000 may perform a function that is preset according to the ID information of the medical apparatus 1000.

For example, if the medical apparatus 1000 is a medical image capturing apparatus, the mobile apparatus 2000 may determine to perform a function of controlling the medical image capturing apparatus or perform a function of displaying a previously captured medical image of an object of which a medical image is being captured, according to an operation mode of the mobile apparatus 2000.

For example, if the medical apparatus 1000 is a console apparatus that controls another medical apparatus, the mobile apparatus 2000 may determine to perform a function of controlling the another medical apparatus that is controlled by the console apparatus or to perform a function of displaying state information of the object, according to an operation mode of the mobile apparatus 2000.

For example, if the medical apparatus 1000 is a medical image display apparatus, the mobile apparatus 2000 may determine to perform a function of controlling the medical image display apparatus or to perform a function of displaying a medical record of the object, according to an operation mode of the mobile apparatus 2000.

In operation S250, the mobile apparatus 2000 may perform the at least one determined function.

The at least one determined function may include a function of controlling the medical apparatus 1000.

For example, the mobile apparatus 2000 may perform a remote controller function of the medical apparatus 1000. The mobile apparatus 2000 may receive the type, model name, or intrinsic identifier of the medical apparatus 1000 from the medical apparatus 1000. The mobile apparatus 2000 may display a GUI that operates as a control panel of the medical apparatus 1000, based on the ID information of the medical apparatus 1000. Also, the mobile apparatus 2000 may display a GUI on a touch screen of the medical apparatus 1000. Also, the mobile apparatus 2000 may receive an image including a medical image displayed on the touch screen of the medical apparatus 1000, and display the image on the screen of the mobile apparatus 2000. Here, the mobile apparatus 2000 may transmit coordinate information corresponding to a user input on the touch screen to control the medical apparatus 1000 to perform a function according to the user input.

For example, the mobile apparatus 2000 may transmit and/or receive control information for directly controlling the medical apparatus 1000 to and/or from the medical apparatus 1000 to perform a function of controlling the medical apparatus 1000. The mobile apparatus 2000 may receive the ID information of the medical apparatus 1000, as well as a function currently performed by the medical apparatus 1000 and information needed to perform the function. The mobile apparatus 2000 may execute a module for controlling the medical apparatus 1000, which is preset, based on the received information.

For example, if the mobile apparatus 2000 is connected to an MRI apparatus that captures a magnetic resonance (MR) image, the mobile apparatus 2000 may receive a model name of the MRI apparatus, information about MR imaging, and a protocol set by a user, form the MRI apparatus. The mobile apparatus 2000 may execute a module for controlling the MRI apparatus, which is preset, based on received information. Here, the mobile apparatus 2000 may execute the module for controlling the MRI apparatus to receive a control command regarding the MRI apparatus from the user. The mobile apparatus 2000 may transmit control information to the MRI apparatus based on received input information to control the MRI apparatus to perform a function based on a user input.

Also, the at least one determined function may include a function of displaying the object-related information.

The mobile apparatus 2000 may display a GUI for providing the object-related information. The mobile apparatus 2000 may receive the object-related information from the medical apparatus 1000 or an external server and display the object-related information on the screen, based on a user input through the GUI.

For example, the mobile apparatus 2000 may display patient-related information about a patient of which an image is being captured or displayed by the medical apparatus 1000. The patient-related information may include a medical record of the patient, a medical image of the patient, or a state of the patient during imaging.

For example, the mobile apparatus 2000 may receive and display, on the screen, ID information of the patient from the medical apparatus 1000. Also, the mobile apparatus 2000 may receive and display, on the screen, the medical record and medical image of the patient from a server, such as a PACS, in which the patient-related information is stored, based on the ID information of the patient that is pre-stored and/or received from the medical apparatus 1000. For example, the mobile apparatus 2000 that is connected to an ultrasound apparatus capturing an ultrasound image of breasts of the patient may receive the ID information of the patient from the ultrasound apparatus. The mobile apparatus 2000 may receive and display, on the screen, an X-ray image of the breasts of the patient captured via mammography, by using the ID information of the patient.

According to exemplary embodiments described above, the user may view a medical image of the user or receive information needed for diagnosis in real-time, without using a separate display apparatus.

Also, for example, the mobile apparatus 2000 may receive and display, on the screen, state information of the patient being imaged, progress information of imaging, and medical image information, from the medical apparatus 1000. For example, the mobile apparatus 2000 may be connected to the MRI apparatus that captures an MR image. The mobile apparatus 2000 may receive and display, on the screen, the state information of the patient, which includes, for example, a heart rate, a temperature, and a brainwave of the patient being imaged, a capturing protocol of an MR image being captured, or a captured MR image, from the MRI apparatus.

Also, for example, the mobile apparatus 2000 may display lesion information of the patient of which an image is being captured or displayed by the medical apparatus 1000. The lesion information may include medical information about a lesion. The mobile apparatus 2000 may receive lesion information of the patient of which an image is being captured or displayed from the medical apparatus 1000, and display, on the screen, medical information about a lesion.

Before performing a function, the mobile apparatus 2000 may provide a function of verifying with the user whether to perform the function. For example, the mobile apparatus 2000 may display a confirmation button, on the screen, for confirming whether to perform the function, and may perform the function when the user determines to perform the function, e.g., in response to a user input through the confirmation button.

The mobile apparatus 2000 may display a menu for selecting from a plurality of functions according to an operation mode. The mobile apparatus 2000 may perform at least one function from the plurality of functions based on a user's selection.

The mobile apparatus 2000 may detect an input for changing an operation mode of the mobile apparatus 2000. For example, the mobile apparatus 2000 may receive an input of changing a first operation mode to a second operation mode. The mobile apparatus 2000 may change the first operation mode to the second operation mode based on the input, and perform at least one function corresponding to the second operation mode. For example, if the mobile apparatus 2000 detects that the displacement of the mobile apparatus 2000 changes to be in a width direction through the displacement sensor while displaying the object-related information, the mobile apparatus 2000 may change an operation mode to a width direction mode, and perform a function of controlling the medical apparatus 1000 corresponding to the width direction mode.

Also, if the mobile apparatus 2000 detects the input for changing an operation mode from the first operation mode to the second operation mode, the mobile apparatus 2000 may immediately perform a function corresponding to the second operation mode or verify with the user whether to perform the function corresponding to the second operation mode. For example, the mobile apparatus 2000 may display a confirmation button for confirming whether to perform the function corresponding to the second operation mode, and perform the function corresponding to the second operation mode when the user determines to perform the function corresponding to the second operation mode, e.g., in response to a user input through the confirmation button.

The input for changing an operation mode from the first operation mode to the second operation mode may be received while or before the mobile apparatus 2000 performs a function corresponding to the first operation mode.

Also, if the communication link with the medical apparatus 1000 is terminated, the mobile apparatus 2000 may automatically delete the object-related information received from the medical apparatus 1000 and/or the external server.

The mobile apparatus 2000 may receive medical information from a server, such as PACS, EMR, PHR, or RIS, in which medical-related information is stored, by using a wireless network in a hospital. Here, the mobile apparatus 2000 may perform an authorization process for accessing the medical information, and the mobile apparatus 2000 that is authorized may receive the medical information.

An access to the medical information may be limited to the mobile apparatus 2000 located inside the hospital. For example, the mobile apparatus 2000 and the medical apparatus 1000 may each include a global positioning system (GPS). The mobile apparatus 2000 may operate to receive the medical information when a location of the mobile apparatus 2000, which is obtained via the GPS, is determined to be inside the hospital.

The medical apparatus 1000 may transmit the medical image information or the ID information of the object to the mobile apparatus 2000 based on a request from the mobile apparatus 2000. Also, the medical apparatus 1000 may request the mobile apparatus 2000 for authorization information, and transmit the medical image information or the ID information of the object to the mobile apparatus 2000 when authentication is completed.

FIGS. 3A, 3B, 3C, and 3D are diagrams for describing a method of controlling the medical apparatus 1000 according to an operation mode of the mobile apparatus 2000, according to an exemplary embodiment.

As shown in FIG. 3A, the mobile apparatus 2000 may be connected to the medical apparatus 1000 to perform a function of controlling the medical apparatus 1000.

The mobile apparatus 2000 may be connected to a port (not shown) included in the medical apparatus 1000, or mounted on an expansion slot (not shown) of the medical apparatus 1000. In an exemplary embodiment, if a communication link is formed between the mobile apparatus 2000 and the medical apparatus 1000 via wires, the mobile apparatus 2000 may operate dependently upon the medical apparatus 1000.

In another exemplary embodiment, the mobile apparatus 2000 may form the communication link with the medical apparatus 1000 via short-range wireless communication. For example, the mobile apparatus 2000 and the medical apparatus 1000 may form a short-range wireless communication link via, for example, NFC communication or WFD communication. For example, the mobile apparatus 2000 and the medical apparatus 1000 may each include an NFC module and perform NFC communication therebetween.

When the mobile apparatus 2000 is connected to the medical apparatus 1000 via wires or short-range wireless communication, an operation mode of the mobile apparatus 2000 may be detected and at least one function corresponding to the detected operation mode may be determined.

The mobile apparatus 2000 may display a GUI 350 to verify with the user whether to perform the at least one determined function, and perform the at least one determined function when the user determines to perform the at least one determined function.

Also, the mobile apparatus 2000 may perform a remote controller function of the medical apparatus 1000. The mobile apparatus 2000 may display a GUI 360 for performing functions of a control panel 1100 of the medical apparatus 1000 based on the type, model name, and/or intrinsic identifier of the medical apparatus 1000, which are received from the medical apparatus 1000. The mobile apparatus 2000 may transmit a coordinate value according to the user input to the medical apparatus 1000. Alternatively, the mobile apparatus 2000 may convert the coordinate value to an ID value of a button on the control panel 1100, and transmit the ID value to the medical apparatus 1000. Accordingly, the user may manipulate the medical apparatus 1000 by selecting a button image corresponding to the button of the control panel 1100 in the GUI 360, which is displayed on the screen of the mobile apparatus 2000.

Also, the mobile apparatus 2000 may execute a module for controlling the medical apparatus 1000 based on information received from the medical apparatus 1000. The mobile apparatus 2000 may display a GUI 370 for executing the module for controlling the medical apparatus 1000. For example, the mobile apparatus 2000 may display the GUI 370 for performing functions of a control panel 1400 of the medical apparatus 1000. Accordingly, the mobile apparatus 2000 may transmit and/or receive control information for directly controlling the medical apparatus 1000 to and/or from the medical apparatus 1000, thereby controlling the medical apparatus 1000.

For example, if the medical apparatus 1000 is an ultrasound apparatus and the user selects a motion mode (or M-mode) image, the mobile apparatus 2000 may display a GUI for setting the M-mode image. In this case, the mobile apparatus 2000 may transmit a parameter value set by the user to the ultrasound apparatus, and transmit control information selected by the user to the ultrasound apparatus.

Figure 4B:
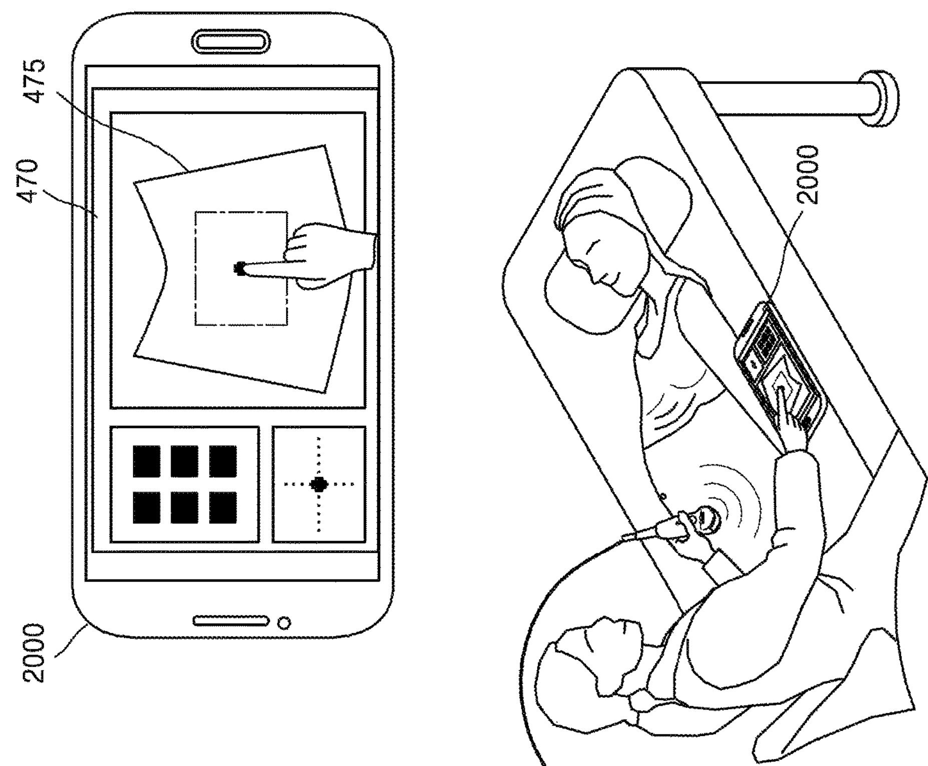
FIGS. 4A and 4B are diagrams for describing a method of controlling a medical apparatus according to an operation mode of a mobile apparatus, according to another exemplary embodiment.
Figure 4A:
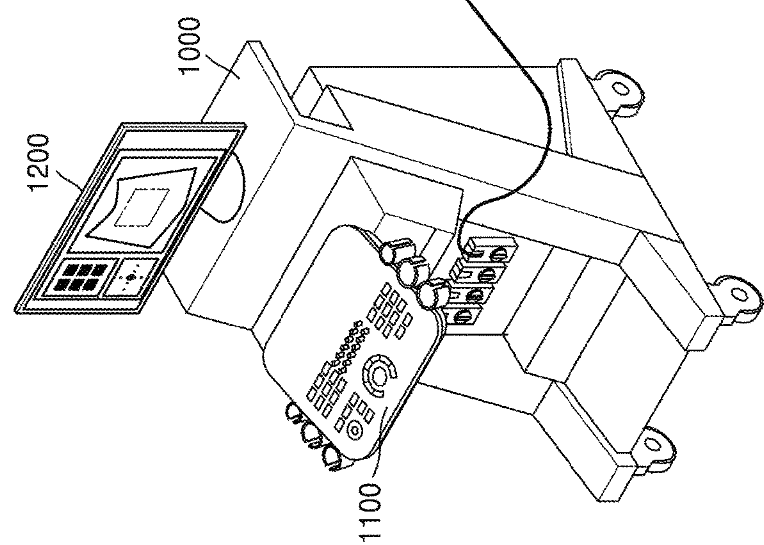

FIGS. 4A and 4B are diagrams for describing a method of controlling the medical apparatus 1000 according to an operation mode of the mobile apparatus 2000, according to another exemplary embodiment.

As shown in FIGS. 4A and 4B, the mobile apparatus 2000 may receive and display, on the screen, a GUI 470 displayed on the touch screen of the medical apparatus 1000, from the medical apparatus 1000. Also, the mobile apparatus 2000 may receive and display, on the screen, a medical image 475 displayed on a touch screen of the medical apparatus 1000. Here, the mobile apparatus 2000 may transmit coordinate information corresponding to a user input on the touch screen to the medical apparatus 1000 to control the medical apparatus 1000 to perform a function according to the user input.

As described above, according to exemplary embodiments, the user may capture a medical image, e.g., an ultrasound image, while controlling the medical apparatus 1000 by using the mobile apparatus 2000 even when the user is located further away from the medical apparatus 1000.

Figure 5B:
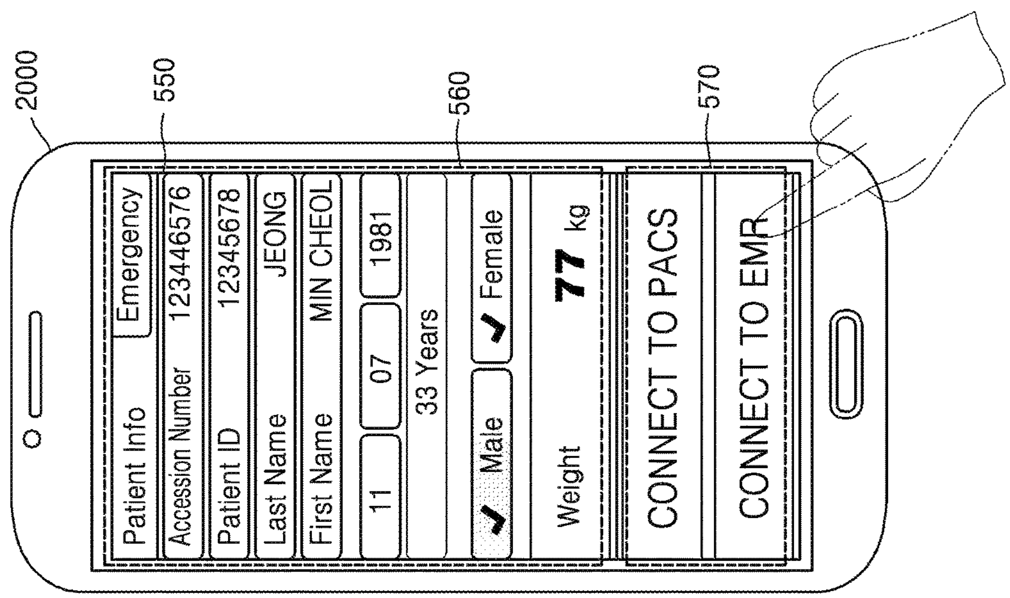
FIGS. 5A and 5B are diagrams for describing a method of displaying object-related information according to an operation mode of a mobile apparatus, according to an exemplary embodiment.
Figure 5A:
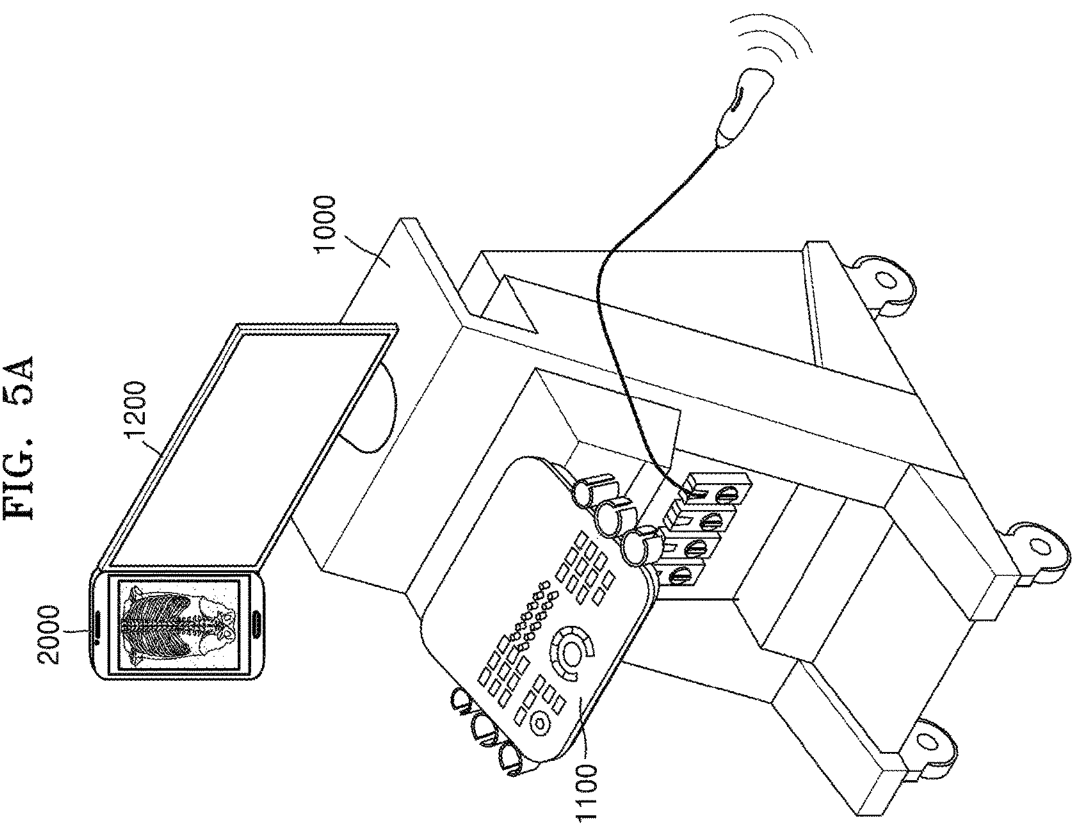

FIGS. 5A and 5B are diagrams for describing a method of displaying object-related information according to an operation mode of the mobile apparatus 2000, according to an exemplary embodiment.

As shown in FIGS. 5A and 5B, the medical apparatus 1000 may include a monitor having a docking system (not shown). The mobile apparatus 2000 may be mounted on the docking system included in the medical apparatus 1000. Also, the mobile apparatus 2000 may form a communication link with the medical apparatus 1000 via, for example, short-range wireless communication. For example, the mobile apparatus 2000 and the medical apparatus 1000 may form a short-range wireless communication link via, for example, NFC communication or WFD communication.

As shown in FIG. 5B, the mobile apparatus 2000 may display a GUI 550 for providing the object-related information. The mobile apparatus 2000 may receive and display, on the screen, the object-related information from the medical apparatus 1000 or an external server, based on a user input received through the GUI 550.

The mobile apparatus 2000 may display patient-related information 560 about a patient of which an image is being captured or displayed by the medical apparatus 1000. The patient-related information 560 may include a medical record of the patient, a medical image of the patient, or a state of the patient being imaged.

The mobile apparatus 2000 may receive ID information of the patient from the medical apparatus 1000. The mobile apparatus 2000 may receive the medical record or medical image of the patient from a server such as PACS in which medical-related information of the patient is stored, based on the ID information of the patient, which is pre-stored and/or received from the medical apparatus 1000. For example, the mobile apparatus 2000 may connect to the server such as PACS or EMR based on a user input through a menu 570 on the GUI 550.

Accordingly, a user may image or diagnose the patient while looking at the medical record or medical image of the patient, and may obtain information needed for imaging or diagnosing the patient in real-time without using a separate display apparatus.

Figure 6:
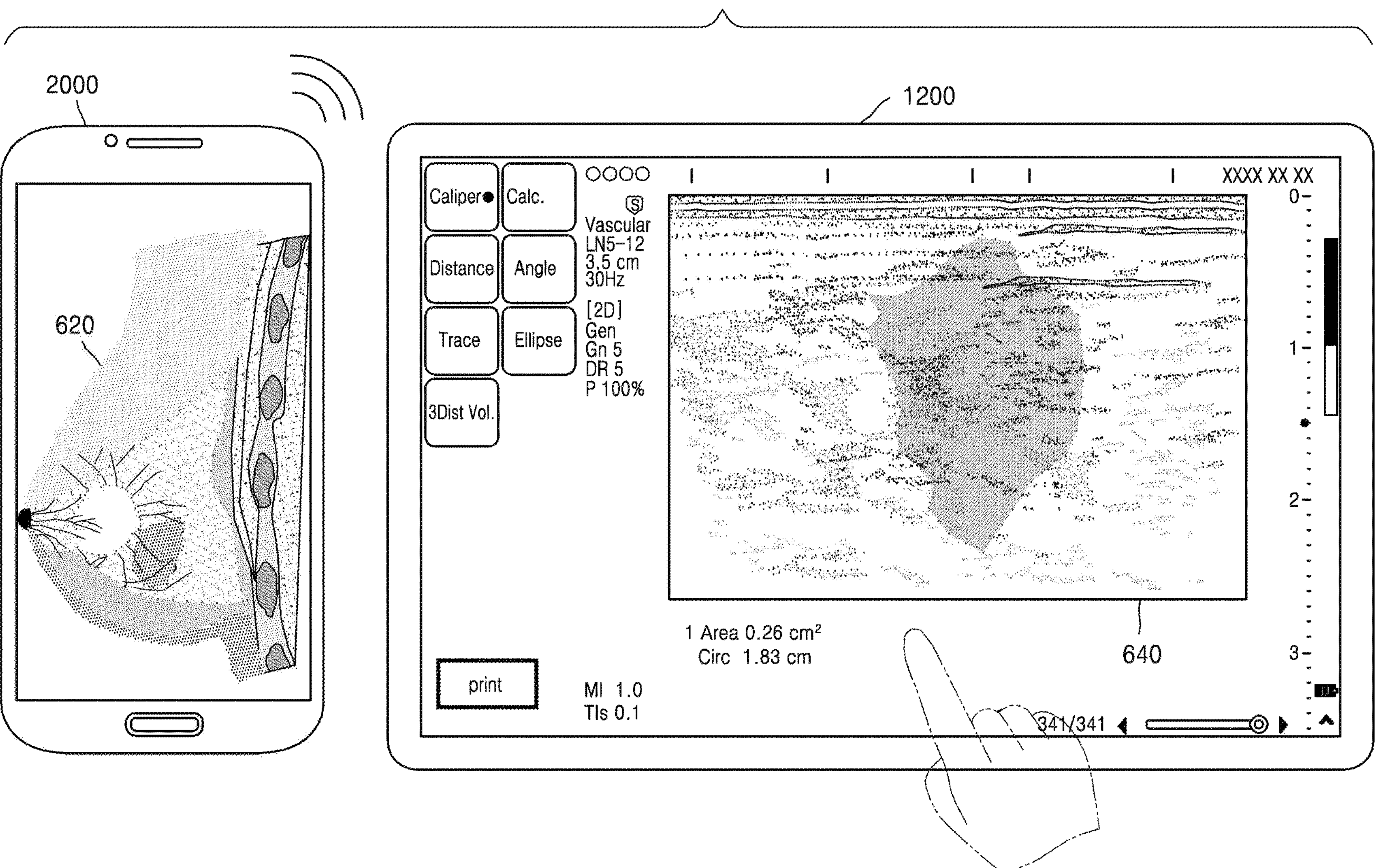
FIG. 6 is a diagram for describing a method of displaying object-related information according to an operation mode of a mobile apparatus, according to another exemplary embodiment.

FIG. 6 is a diagram for describing a method of displaying object-related information according to an operation mode of the mobile apparatus 2000, according to another exemplary embodiment.

As shown in FIG. 6, the mobile apparatus 2000 may be connected to an ultrasound apparatus 1000 that captures a breast ultrasound image 640 of a patient. The mobile apparatus 2000 may receive ID information and lesion information of the patient from the ultrasound apparatus 1000. The mobile apparatus 2000 may receive a breast X-ray image 620 of the patient captured via mammography, by using the ID information and lesion information of the patient.

For example, the mobile apparatus 2000 may receive the breast X-ray image 620 from a medical image storage server (not shown) by using ID and authorization information of the patient. The mobile apparatus 2000 may display the received breast X-ray image 620 on the screen of the mobile apparatus 2000.

The mobile apparatus 2000 may automatically request the medical image storage server for a medical image (e.g., the breast X-ray image 620) when the communication link is formed with the medical apparatus 1000. Also, the mobile apparatus 2000 may request the medical image storage server for a medical image based on a user input requesting for a medical image.

FIGS. 7A, 7B, 7C, and 7D are diagrams for describing a method of determining a function to be performed according to displacement of the mobile apparatus 2000, according to exemplary embodiments.

As shown in FIG. 7A through 7D, the medical apparatus 1000 may include an expansion slot 1300 that may rotate. Also, the mobile apparatus 2000 may determine an operation mode based on a direction of the mobile apparatus 2000 mounted on the control panel 1100. Also, the mobile apparatus 2000 may change an operation mode when the direction of the mobile apparatus 2000, which is mounted on the control panel 1100, changes. For example, when the expansion slot 130 of the medical apparatus 1000, on which the mobile apparatus 2000 is mounted, is rotated such that the direction of the mobile apparatus 2000 changes, the operation mode of the mobile apparatus 2000 is changed accordingly.

For example, as shown in FIG. 7A, the mobile apparatus 2000 may perform a function of controlling the medical apparatus 1000 (e.g., an ultrasound apparatus) when mounted, in a width direction, on the expansion slot 1300 included in the control panel 1100 of the medical apparatus 1000. Here, as shown in FIG. 7B, when the expansion slot 1300 included in the control panel 1100, on which the mobile apparatus 2000 is mounted, may be erected in a height direction, the mobile apparatus 2000 mounted on the expansion slot 1300 may detect that a direction of the mobile apparatus 2000 is changed to a height direction via, for example, a displacement sensor. Accordingly, the mobile apparatus 2000 may perform a function corresponding to a height direction mode of the mobile apparatus 2000, e.g., displaying a medical image of an object, which is captured via another modality (for example, X-ray) and stored in an external server, while performing the function of controlling the medical apparatus 1000.

As shown in FIG. 7C, the mobile apparatus 2000 may perform the function of displaying the medical image captured via the another modality and stored in the external server, when mounted on the expansion slot 1300 in the height direction. Here, as shown in FIG. 7D, when the expansion slot 1300 included in the control panel 1100, on which the mobile apparatus 2000 is mounted, may be erected in the height direction, and the mobile apparatus 2000 mounted on the expansion slot 1300 may detect that the direction of the mobile apparatus 2000 changes to the width direction via the displacement sensor. Accordingly, the mobile apparatus 2000 may perform the function of controlling the medical apparatus 1000, which is a function corresponding to a width direction mode, while displaying the medical image.

Figure 8B:
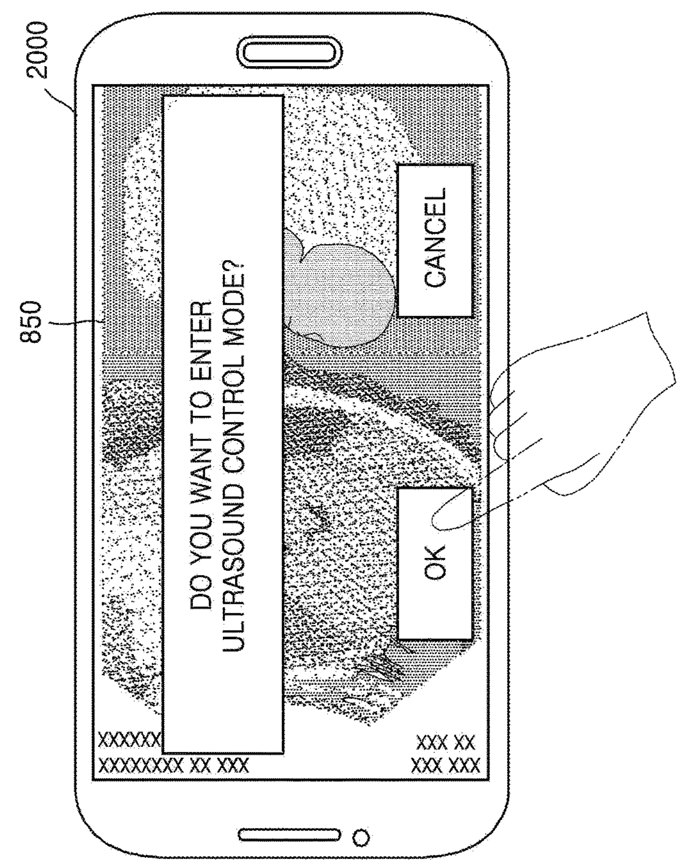
FIGS. 8A and 8B are diagrams for describing a method of determining an operation mode according to displacement of a mobile apparatus, according to exemplary embodiments.
Figure 8A:
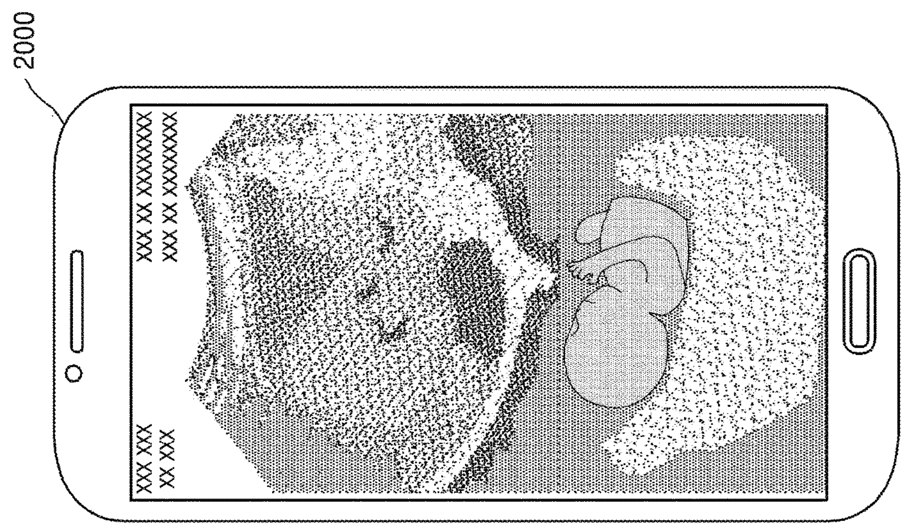

FIGS. 8A and 8B are diagrams for describing a method of determining an operation mode according to displacement of the mobile apparatus 2000, according to exemplary embodiments.

As shown in FIG. 8A, the mobile apparatus 2000 may display a medical image captured by an ultrasound apparatus by being connected to the ultrasound apparatus. That is, in FIG. 8A, the mobile apparatus 2000 is in a height direction and displays the medical image according to a height direction mode.

As shown in FIG. 8B, when a direction of the mobile apparatus 2000 changes to a width direction as shown in FIG. 8B, the mobile apparatus 2000 may display a GUI 850 for a user to determine whether to perform a function of controlling the ultrasound apparatus. Here, the mobile apparatus 2000 may operate to perform the function of controlling the ultrasound apparatus when the user determines to perform the function.

Figure 9A:
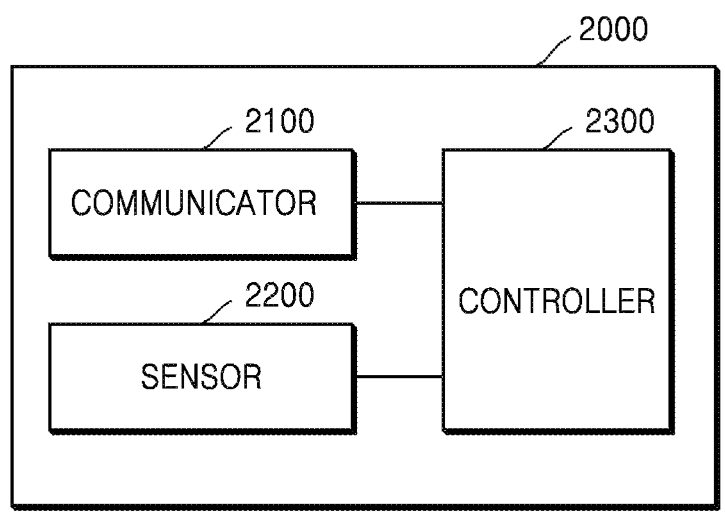
FIGS. 9A and 9B are block diagrams of a mobile apparatus according to exemplary embodiments.
Figure 9B:
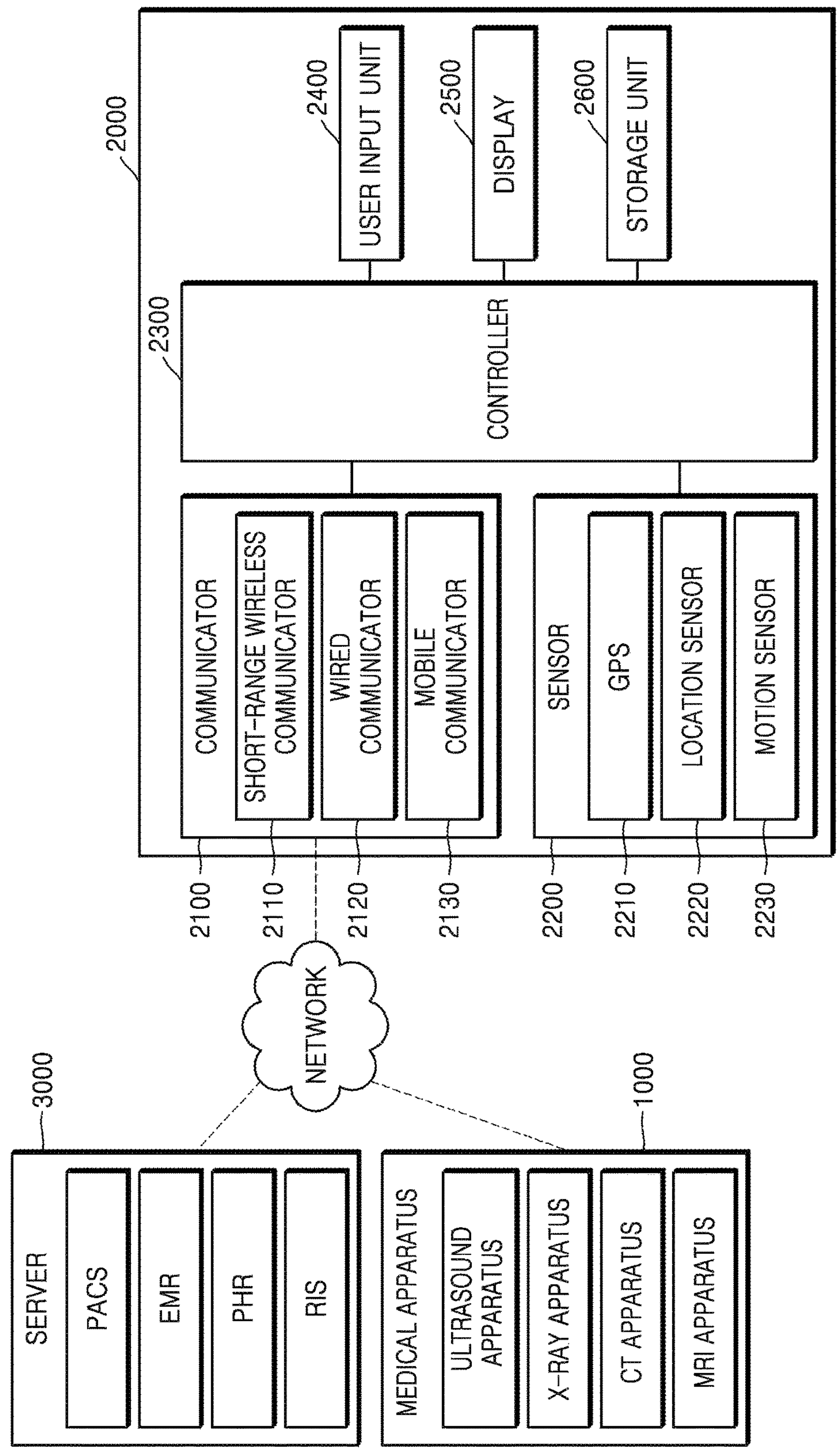

FIGS. 9A and 9B are block diagrams of the mobile apparatus 2000 according to exemplary embodiments.

As shown in FIG. 9A, the mobile apparatus 2000 may include a communicator 2100, a sensor 2200, and a controller 2300. However, not all components shown in FIG. 9A may be essential. For example, the mobile apparatus 2000 may include more or less components than those shown in FIG. 9A. For example, as shown in FIG. 9B, the mobile apparatus 2000 may further include a user input unit 2400, a display 2500, and a storage unit 2600, as well as the communicator 2100, the sensor 2200, and the controller 2300.

The components of the mobile apparatus 2000 will now be described in detail.

The communicator 2100 may be connected to the medical apparatus 1000 and a server 3000 via any one of various communication methods.

The communicator 2100 may include a short-range wireless communicator 2110, a wired communicator 2120, and a mobile communicator 2130. Examples of the short-range wireless communicator 2110 include a Bluetooth communicator, a BLE communicator, an NFC unit, a WLAN (e.g., Wi-Fi) communicator, a Zigbee communicator, an IrDA communicator, a WFD communicator, a UWB communicator, and an Ant+ communicator, but are not limited thereto.

The wired communicator 2120 may be connected to the medical apparatus 1000 and the server 3000 via wires. The wired communicator 2120 may be connected to a port, an expansion slot, or a network interface (for example, LAN) included in the medical apparatus 1000 via wires.

The sensor 2200 may detect an operation mode of the mobile apparatus 2000 by using a displacement sensor included in the mobile apparatus 2000.

The sensor 2200 may include the displacement sensor, such as a global positioning system (GPS) 2210, a location sensor 2220, and a motion sensor 2230. The motion sensor 2230 may include an accelerometer, a gravity sensor, a gyroscope, or a rotational vector sensor. The location sensor 2220 may include an orientation sensor or a magnetometer.

The controller 2300 may determine at least one function corresponding to an operation mode of the mobile apparatus 2000 detected from among functions provided by the medical apparatus 1000. In an exemplary embodiment, the controller 2300 may be a processor.

For example, if an operation mode of the mobile apparatus 2000 is a width direction mode, the controller 2300 may determine to perform a function of controlling the medical apparatus 1000 forming a communication link with the mobile apparatus 2000. Also, if an operation mode of the mobile apparatus 2000 is a height direction mode, the controller 2300 may determine to perform a function of displaying object-related information about an object of which an image is being captured or displayed by the medical apparatus 1000.

In another example, if an operation mode of the mobile apparatus 2000 is a width direction mode, the controller 2300 may determine to perform a function of displaying the object-related information about the object of which an image is being captured or displayed by the medical apparatus 1000. Also, if an operation mode of the mobile apparatus 2000 is a height direction mode, the controller 2300 may determine to perform a function of controlling the medical apparatus 1000 forming the communication link with the mobile apparatus 2000.

Also, the controller 2300 may determine the at least one function by further considering ID information of the medical apparatus 1000. The ID information of the medical apparatus 1000 may include a type, model name, or intrinsic identifier of the medical apparatus 1000. The controller 2300 may receive the ID information of the medical apparatus 1000 from the medical apparatus 1000 via the communication link.

For example, if the medical apparatus 1000 is a medical image capturing apparatus, the controller 2300 may determine to perform a function of controlling the medical image capturing apparatus or a function of displaying a previously captured medical image of the object which is being imaged, according to an operation mode of the mobile apparatus 2000.

For example, if the medical apparatus 1000 is a console apparatus that controls another medical apparatus, the controller 2300 may determine to perform a function of controlling the another medical apparatus controlled by the console apparatus or a function of displaying state information of the object, according to an operation mode of the mobile apparatus 2000.

For example, if the medical apparatus 1000 is a medical image display apparatus, the controller 2300 may determine to perform a function of controlling the medical image display apparatus or a function of displaying a medical record of the object, according to an operation mode of the mobile apparatus 2000.

Also, the controller 2300 may perform the at least one determined function.

For example, the controller 2300 may perform a remote controller function of the medical apparatus 1000. The controller 2300 may receive the type, model name, and intrinsic identifier of the medical apparatus 1000 from the medical apparatus 1000. The controller 2300 may display a GUI that is displayed on the touch screen of the medical apparatus 1000, based on the ID information of the medical apparatus 1000. Also, the controller 2300 may receive and display, on the screen of the mobile apparatus 2000, an image including a medical image being displayed on the touch screen of the medical apparatus 1000. Here, the controller 2300 may transmit coordinate information corresponding to a user input on the touch screen to the medical apparatus 1000 to control the medical apparatus 1000 to perform a function according to the user input.

Also, for example, the controller 2300 may transmit and/or receive control information for directly controlling the medical apparatus 1000 to and/or from the medical apparatus 1000 to perform a function of controlling the medical apparatus 1000. The controller 2300 may receive the ID information of the medical apparatus 1000, as well as a function being currently performed by the medical apparatus 1000 and information needed to perform the function. The mobile apparatus 2000 may execute a module for controlling the medical apparatus 1000, which is preset, based on received information.

The controller 2300 may display a GUI for providing object-related information. The controller 2300 may receive and display, on the screen, the object-related information from the medical apparatus 1000 or an external server (e.g., the server 3000), based on a user input through the GUI.

For example, the controller 2300 may display patient-related information about a patient of which an image is being captured or displayed by the medical apparatus 1000. The patient-related information may include a medical record of the patient, a medical image of the patient, and a state of the patient being imaged.

Also, for example, the controller 2300 may receive and display, on the screen, state information of the patient being imaged, progress information of imaging, and captured medical image information, from the medical apparatus 1000. For example, the controller 2300 may be connected to an MRI apparatus that captures an MR image. The controller 2300 may receive and display, on the screen, state information of the patient, such as a heart rate, temperature, and brainwaves of the patient, an imaging protocol of an MR image, or a captured MR image, from the MRI apparatus.

Also, for example, the controller 2300 may display lesion information of the patient of which an image is being captured or displayed by the medical apparatus 1000. The lesion information may include medical information about a lesion. The controller 2300 may receive lesion information of the patient of which an image is being captured or displayed from the medical apparatus 1000, and display medical information about the lesion on the screen.

Before performing a function, the controller 2300 may provide a function of verifying with a user whether to perform the function. The controller 2300 may display a confirmation button for the user to confirm whether to perform the function, and perform the function when the user determines to perform the function, e.g., in response to a user input through the confirmation button.

The controller 2300 may display a menu for selecting at least one function from a plurality of functions according to an operation mode. The controller 2300 may perform at least one function from the plurality of functions based on a user selection.

The controller 2300 may detect an input for changing an operation mode of the mobile apparatus 2000. For example, the mobile apparatus 2000 may receive an input for changing a first operation mode to a second operation mode. The mobile apparatus 2000 may change the first operation mode of the mobile apparatus 200 to the second operation mode based on the detected input, and perform at least one function corresponding to the second operation mode. For example, if it is detected that the displacement of the mobile apparatus 2000 is changed to a width direction via the displacement sensor while the mobile apparatus 2000 displays the object-related information, the controller 2300 may change an operation mode of the mobile apparatus 2000 to a width direction mode and perform a function corresponding to the width direction mode, e.g., controlling the medical apparatus 1000.

Also, if the input for changing the first operation mode to the second operation mode is detected, the controller 2300 may immediately perform a function corresponding to the second operation mode or may additionally verify with the user whether to perform the function corresponding to the second operation mode. For example, the controller 2300 may display a confirmation button for a user to determine whether to perform the function corresponding to the second operation mode, and perform the function when the user determines to perform the function, e.g., in response to a user input through the confirmation button.

The input for changing the first operation mode of the mobile apparatus 2000 may be received while or before the mobile apparatus 2000 performs a function corresponding to the first operation mode.

Also, if the communication link formed with the medical apparatus 1000 according to wired communication or short-range wireless communication is terminated, the controller 2300 may automatically delete the object-related information received from the medical apparatus 1000 or the external server (e.g., the server 3000).

The user input unit 2400 may be used by the user to input data for controlling the medical apparatus 1000 or for transmitting and/or receiving information to and/or from the external server (e.g., the server 3000). Examples of the user input unit 2400 include a keypad, a dome switch, a touch pad including, for example, a contact capacitance type, a pressure resistance film type, an infrared light detecting type, a surface ultrasound conducting type, an integral tension measuring type, and/or a piezo-effect type, a jog wheel, and/or a jog switch, but are not limited thereto. In an exemplary embodiment, the user input unit 2400 may be a touch screen including a touch pad and a display panel wherein the touch pad forms a layer structure with the display panel.

The display 2500 may display information transmitted and/or received between the mobile apparatus 2000 and the medical apparatus 1000 or the external server (e.g., the server 3000). Also, the display 2500 may display a GUI for receiving information from the medical apparatus 1000 or the external server (e.g., the server 3000). The display 2500 may be used as an input device, as well as an output device.

The storage unit 2600 may store information the mobile apparatus 2000 transmits and/or receives to and/or from the medical apparatus 1000 or the external server (e.g., the server 3000) by interworking with the medical apparatus 1000 or the external server (e.g., the server 3000). Also, the storage unit 2600 may store information needed to interwork with the medical apparatus 1000 or the external server (e.g., the server 3000).

The storage unit 2600 may include at least one storage medium of a flash memory type, a hard disk type, a multimedia card micro type, a card type memory (for example, a secure digital (SD) or extreme digital (XD) memory), a random access memory (RAM) type, a static random access memory (SRAM) type, a read-only memory (ROM) type, an electrically erasable programmable read-only memory (EEPROM) type, a programmable read-only memory (PROM) type, a magnetic memory type, a magnetic disk type, and an optical disk type. Alternatively, the mobile apparatus 2000 may operate a web storage or a cloud server that performs a storage function of the storage unit 2600 on the Internet.

The methods according to the exemplary embodiments described above may be recorded on a computer readable recording medium by being embodied in computer programs executed by using various computers. The computer readable recording medium may include at least one of a program command, a data file, and a data structure. The program commands recorded in the computer readable recording medium may be specially designed or well known to one of ordinary skill in the computer software field. Examples of the computer readable recording medium include read-only memories (ROMs), random-access memories (RAMs), compact-disk (CD)-ROMs, magnetic tapes, floppy disks, optical data storage devices, etc. Examples of the computer command include mechanical codes prepared by a compiler, and/or high-level languages executable by a computer by using an interpreter.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art.

What is claimed is:

1. A method of controlling a medical apparatus, the method comprising:

establishing, by a mobile apparatus, a communication link between the mobile apparatus and the medical apparatus, the mobile apparatus being mounted on a control panel of the medical apparatus;

detecting an operation mode of the mobile apparatus in response to establishing the communication link;

determining a function corresponding to the detected operation mode from functions provided by the medical apparatus; and performing the determined function, wherein the detecting of the operation mode comprises determining the operation mode as one of a width direction mode and a height direction mode based on orientation information of the mobile apparatus, wherein the performing of the determined function comprises, when the operation mode is the width direction mode in which the mobile apparatus is positioned in a width direction, controlling the medical apparatus based on a user input, and wherein the performing of the determined function comprises, when the operation mode is the height direction mode in which the mobile apparatus is positioned in a height direction, displaying object-related information comprising at least one of medical record information of an object, medical image record information of the object, a medical image captured by the medical apparatus, and lesion information of the object.

2. The method of claim 1, further comprising:

receiving an input for changing the operation mode of the mobile apparatus;

changing the operation mode of the mobile apparatus to another operation mode based on the received input; and performing the function corresponding to the another operation mode.

3. The method of claim 1, wherein the performing the determined function comprises:

displaying a confirmation button for confirming whether to perform the determined function; and performing the determined another function, of the functions of the provided by the medical apparatus, based on a user input received via the confirmation button.

4. A non-transitory computer-readable recording medium having recorded thereon a program, which, when executed by a computer, causes the computer to perform the method of claim 1.

5. The method of claim 1, wherein the determining of the function comprises:

receiving identification (ID) information of the medical apparatus, from the medical apparatus, through the communication link; and determining the function based on the received ID information of the medical apparatus.

6. A mobile apparatus for controlling a medical apparatus, the mobile apparatus comprising:

a communicator configured to establish a communication link with the medical apparatus, the mobile apparatus being mounted on a control panel of the medical apparatus;

a sensor configured to detect an operation mode of the mobile apparatus in response to establishing the communication link; and a controller configured to determine a function corresponding to the detected operation mode from functions provided by the medical apparatus, and perform the determined function, wherein the sensor is configured to determine whether the operation mode of the mobile apparatus is a width direction mode or a height direction mode based on orientation information of the mobile apparatus, wherein, when the operation mode of the mobile apparatus is the width direction mode in which the mobile apparatus is positioned in a width direction, the controller is configured to perform a function of controlling the medical apparatus based on a user input, and wherein, when the operation mode of the mobile apparatus is the height direction mode in which the mobile apparatus is positioned in a height direction, the controller is configured to display object-related information comprising at least one of medical record information of the object, medical image record information of the object, a medical image captured by the medical apparatus, and lesion information of the object.

7. The mobile apparatus of claim 6, wherein the sensor is configured to receive an input for changing the operation mode of the mobile apparatus and change the operation mode of the mobile apparatus to another operation mode based on the input, and the controller is configured to perform another function, of the functions of the provided by the medical apparatus, corresponding to the another operation mode.

8. The mobile apparatus of claim 6, wherein the controller is configured to display a confirmation button for confirming whether to perform the determined function, and perform the determined function based on a user input received via the confirmation button.

9. The mobile apparatus of claim 6, wherein the controller is configured to receive identification (ID) information of the medical apparatus, from the medical apparatus, through the communication link, and determine the function based on the received ID information of the medical apparatus.

* * * * *